United States Patent
Avila et al.

(10) Patent No.: US 6,413,219 B1
(45) Date of Patent: Jul. 2, 2002

(54) THREE-DIMENSIONAL ULTRASOUND DATA DISPLAY USING MULTIPLE CUT PLANES

(75) Inventors: Ricardo Scott Avila; Lisa Sobierajski Avila, both of Clifton Park; William Thomas Hatfield, Schenectady, all of NY (US); Brian Peter Geiser, Hartland, WI (US); Vaishali Vilas Kamat, Waukesha, WI (US); Todd Michael Tillman, West Milkaukee, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/524,596

(22) Filed: Mar. 14, 2000

Related U.S. Application Data (63) Continuation-in-part of application No. 09/299,031, filed on Apr. 23, 1999, now Pat. No. 6,102,861.
(60) Provisional application No. 60/127,037, filed on Mar. 31, 1999.

(51) Int. Cl.[7] .............................................. A61B 8/00
(52) U.S. Cl. ..................................... 600/443; 128/916
(58) Field of Search .............................. 600/437, 440, 600/443–447, 453–457; 128/916; 73/625, 626; 345/421–424; 700/178

(56) References Cited

U.S. PATENT DOCUMENTS

| | | | | |
|---|---|---|---|---|
| 5,488,952 A | * | 2/1996 | Schoolman | 178/660.07 |
| 5,682,895 A | * | 11/1997 | Ishiguro | 600/440 |
| 5,706,816 A | | 1/1998 | Mochizuki et al. | 128/660.07 |
| 5,899,863 A | | 5/1999 | Hatfield et al. | 600/443 |
| 5,954,653 A | | 9/1999 | Hatfield et al. | 600/443 |
| 6,019,725 A | | 2/2000 | Vessely et al. | 600/447 |

OTHER PUBLICATIONS

Greenleaf, J.F. et al.: Multidimensional Cardiac Imaging, Dec. 9, 1992, pp. 403–411, p. 407 figure 3, p. 408.
McCann, H.A. et al.: Multidimensional Ultrasonic Imaging for Cardiology, Sep. 1988, pp. 1063–1072, p. 1066, Figure 11, p. 1068.
Johnson, Charles D. et al.: System for Two–Dimensional and Three–Dimensional Imaging of Tubular Structures in the Human Body, Jul. 30, 1998, p. 13, line 6–line 17, p. 15, line 6–p. 16, line 8, p. 17, line 6–line 16, p. 20, line 21–line 30, p. 22, line 1–p. 23, line.
Argiro, Vincent J. et al.: Advanced Diagnostic Viewer, Apr. 23, 1998, Abstract; Figures 13, 16, p. 2 line 19–p. 27, line 12, p. 29, line 28–p. 31, line 25.
Fenstor, Aaron et al.: Three–Dimensional Imaging System, Jun. 5, 1997, p. 22, line 16–line 23, p. 25, line 20–line 25.

* cited by examiner

Primary Examiner—Francis J. Jaworski
Assistant Examiner—Ali M. Imam
(74) Attorney, Agent, or Firm—Jean K. Testa; Jill Breedlove (57) ABSTRACT

A three-dimensional projection image representing a projection of a data volume at a predetermined orientation, three cut plane images representing respective mutually orthogonal planar cuts through the data volume, a graphical representation of the data volume at that orientation and graphical representations of the cut planes are displayed in spaced relationship. Each of the cut planes has a respective positional relationship to the data volume graphic that corresponds to the positional relationship of the respective cut plane to the data volume. The graphical representations are displayed in different colors. Any one of the four images can be active in the sense that images are reconstructed in real-time as a trackball is moved. Which of the four images is active is indicated by displaying the corresponding graphical representation in a color denoting the active state.

21 Claims, 7 Drawing Sheets

FIG. 10

THREE-DIMENSIONAL ULTRASOUND DATA DISPLAY USING MULTIPLE CUT PLANES

RELATED PATENT APPLICATIONS

This application claims the benefit of priority from U.S. Provisional Application Ser. No. 60/127,037 filed on Mar. 31, 1999. This application is also a continuation-in-part application of U.S. patent application Ser. No. 09/299,031 filed on Apr. 23, 1999, now U.S. Pat No. 6,102,861 the disclosure of which is hereby incorporated by reference.

FIELD OF THE INVENTION

This invention generally relates to three-dimensional ultrasound anatomical imaging and, more particularly, to three-dimensional diagnostic imaging of a body by detecting ultrasonic echoes reflected from a scanned volume in the body.

BACKGROUND OF THE INVENTION

Conventional ultrasound scanners create two-dimensional B-mode images of tissue in which brightness of a pixel is based on intensity of the echo return. Alternatively, in a color flow imaging mode, the movement of fluid (e.g., blood) or tissue can be imaged. Measurement of blood flow in the heart and vessels using the Doppler effect is well known. The phase shift of backscattered ultrasound waves may be used to measure velocity of the backscatterers from tissue or blood. The Doppler shift may be displayed using different colors to represent speed and direction of flow. In power Doppler imaging, the power contained in the returned Doppler signal is displayed. Although the following disclosure refers predominantly to B-mode imaging for the sake of brevity, the present invention applies to any mode of ultrasound imaging.

Two-dimensional ultrasound images are often difficult to interpret due to inability of the observer to visualize the two-dimensional representation of the anatomy being scanned. In addition, it may not be possible to acquire the precise view needed to make a diagnosis due to probe geometry or poor access to the area of interest. However, if the ultrasound probe is swept over an area of interest and two-dimensional images are accumulated to form a three-dimensional data volume, the anatomy becomes much easier to visualize for both the trained and untrained observer. Moreover, views which cannot be acquired due to probe geometry or poor access to the area of interest can be reconstructed from the three-dimensional data volume by constructing slices through the volume at the angle that is difficult to obtain.

In order to generate three-dimensional images, the imaging system computer can transform a source data volume retrieved from memory into an imaging plane data set. The successive transformations may involve a variety of projection techniques such as maximum, minimum, composite, surface, or averaged projections made at angular increments, e.g., at 10° intervals, within a range of angles, e.g., +90° to −90°. Each pixel in the projected image includes the transformed data derived by projection onto a given image plane.

In free-hand three-dimensional ultrasound scans, a transducer array (1D to 1.5D) is translated in the elevation direction to acquire a set of image planes through the anatomy of interest. These images can be stored in memory and later retrieved by the system computer for three-dimensional reconstruction. If the spacings between image frames are known, then the three-dimensional volume can be reconstructed with the correct aspect ratio between the out-of-plane and scan plane dimensions. If, however, the estimates of the inter-slice spacing are poor, significant geometric distortion of the three-dimensional object can result.

A conventional ultrasound imaging system collects B-mode, color flow mode and power Doppler mode data in a cine memory on a continuous basis. As the probe is swept over an area of the anatomy, using either a free-hand scanning technique or a mechanical probe mover, a three-dimensional volume is stored in the cine memory. The distance that the probe was translated may be determined by any one of a number of techniques. The user can provide an estimate of the distance swept. If the probe is moved at a constant rate by a probe mover, the distance can be easily determined. Alternatively, a position sensor can be attached to the probe to determine the position of each slice. Markers on the anatomy or within the data can also provide the required position information. Yet another way is to estimate the scan plane displacements directly from the degree of speckle decorrelation between successive image frames.

If the ultrasound probe is swept over an area of a body (either by hand or by a probe mover) such that the inter-slice spacing is known, and if the slices are stored in memory, a three-dimensional data volume can be acquired. The data volume can be used to form a three-dimensional view of the area. of interest. In addition, the data can be reformatted to produce individual slices at arbitrary angles, thus allowing the user to get the exact view desired regardless of the anatomy under investigation.

The problem that arises is how to display the information in a way that makes it is easy for the observer to relate the two-dimensional slice to the three-dimensional anatomy. Commonly assigned Avila et al. U.S. Pat. No. 5,934,288, issued Aug. 10, 1999, discloses a system with multiple three-dimensional imaging modes that allow the user to view the data as a volume projection, or as individual slices at an arbitrary angle and location in the data volume. This allows the user to obtain any single slice desired and to scroll through the anatomy at that angle. Pat. No. 5,934,288 is hereby incorporated by reference. It is often desirable, however, to visualize how a slice through the data volume relates to non-parallel (e.g., orthogonal) slices through the same point in the data volume.

SUMMARY OF THE INVENTION

In an ultrasound imaging system which scans a human body and collects multiple images (e.g., B mode) in memory to form a data volume derived from a three-dimensional object volume, an image representing that data volume is displayed, accompanied by a plurality of images representing individual slices taken at different angles and intersecting at a point in the data volume. In a preferred embodiment, three images representing mutually orthogonal slices in the data volume are displayed. The display mode is hereinafter referred to as the "orthogonal cut plane" mode. However, those skilled in the pertinent art will readily appreciate that the cut planes need not be mutually orthogonal.

After acquiring a data volume and defining a region of interest, the user enters the orthogonal cut plane mode. This mode may be one of multiple three-dimensional imaging modes or it may be the sole three-dimensional imaging mode. If multiple modes exist, preferably the initial mode on entry to the three-dimensional imaging mode is the orthogonal cut plane mode. The initial mode as well as the sequence of progression from one mode to the next are set in software.

Those skilled in the pertinent art will readily appreciate that the orthogonal cut plane mode need not be the initial mode.

The orthogonal cut plane mode provides the user with a projection of the data volume along with three orthogonal cut planes through the data volume. In addition, an orientation box is displayed to aid the user in visualizing the data volume orientation and the position of the slices in the data volume, and to identify which one of the four displays can be manipulated with the trackball (hereinafter referred to as the "active" display). When the orthogonal cut plane mode is initially entered, the volume projection is active and the orientation box is therefore shown in green and the cut planes are each displayed in a different color (e.g., red, blue and yellow). Additionally, each cut plane display is framed in its corresponding color. When the user manipulates the trackball, the data volume projection is updated in real time. Pressing the "cursor" key changes the "active" display to the next one in sequence and changes its frame to green. At the same time the wire frame for the volume projection changes to white. Manipulating the trackball when one of the cut planes is active allows the user to scroll through the data volume in the selected orientation.

DETAILED DESCRIPTION OF THE INVENTION

The invention is herein disclosed in the context of a B-mode ultrasound imaging system; however, it should be appreciated that the invention has applicability in other ultrasound imaging modes, e.g., velocity or power flow imaging.

Figure 1:
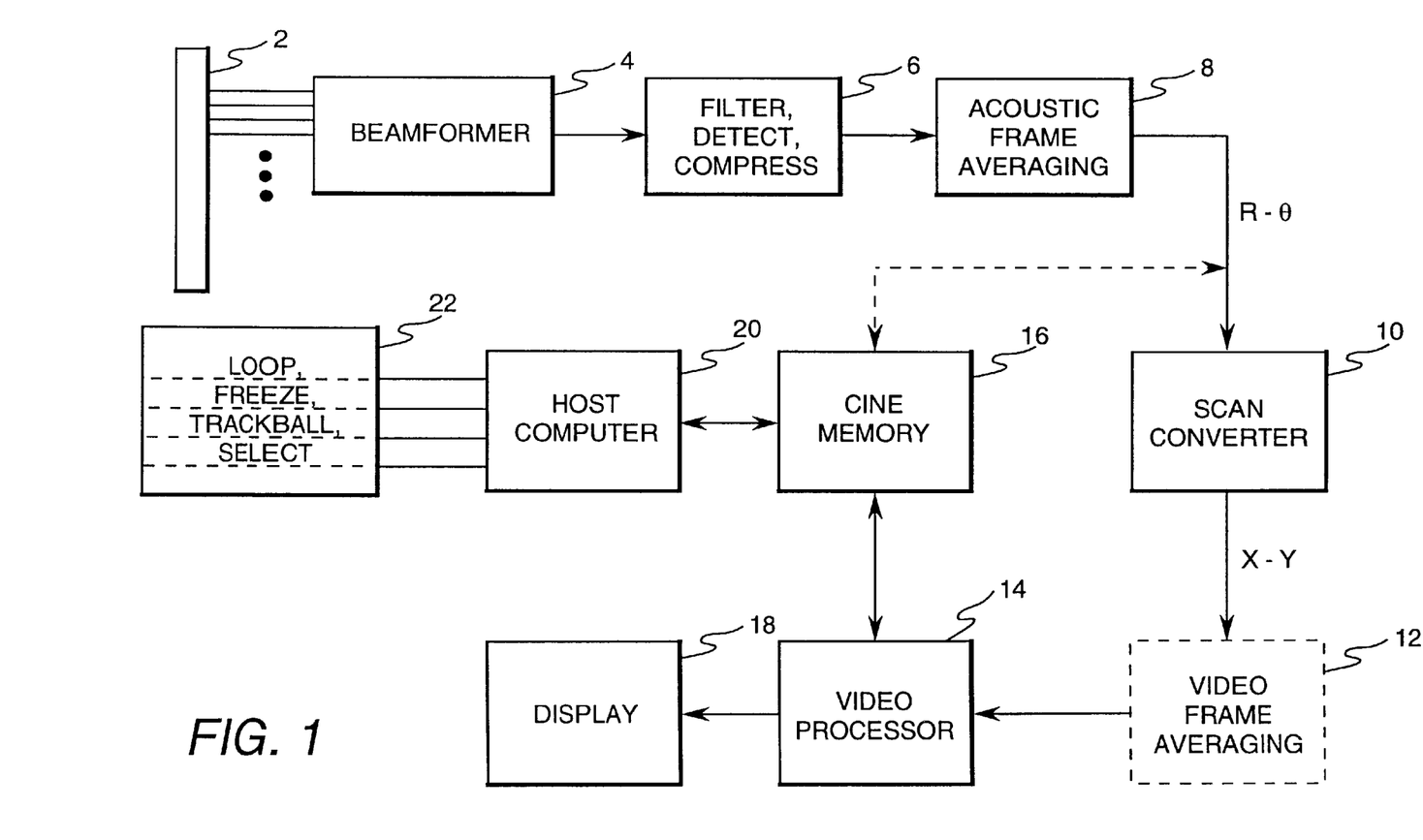
FIG. 1 is a block diagram generally depicting subsystems of a real-time digital ultrasound imaging system programmed with a display mode in accordance with a preferred embodiment of the invention.

The basic signal processing chain in a B-mode imaging system is depicted in FIG. 1. An ultrasound probe 2 incorporating an array of transducer elements is activated to transmit an ultrasound beam focused at a transmit focal position. The return ultrasound signals are detected by the transducer elements and then dynamically focused at successive ranges along a scan line by the beamformer 4 to form a receive vector. The beamformer output data, in the form of electrical signals, for each scan line are passed through a B-mode processing chain 6 which includes equalization filtering, envelope detection and logarithmic compression. Depending on the scan geometry, up to several hundred vectors may be used to form a single acoustic image frame. To smooth the temporal transition from one acoustic frame to the next, some acoustic frame averaging may be performed by an averaging system 8 before scan conversion. For a sector scan, compressed images in $R$-$_\theta$ format are converted by a scan converter 10 into X-Y format for display. On some systems, frame averaging may be performed on the X-Y data by a video frame averager 12 (indicated by a dashed block) rather than on the acoustic frames before scan conversion, and sometimes duplicate video frames may be inserted between acoustic frames in order to achieve a given or desired video display frame rate. In any event, the scan-converted frames are passed to a video processor 14, which basically maps the scan-converted data to a display 18 that provides grayscale mapping for video display of B-mode imaging data.

System control is centered in a host computer 20, which accepts operator inputs through an operator interface 22 and in turn controls the various subsystems. (In FIG. 1, the system control lines from the host computer to the various subsystems are omitted for the sake of simplicity of illustration.) During imaging, a long sequence of the most recent images is stored and continuously updated automatically in a cine memory 16. Some systems are designed to save the $R$-$_\theta$ acoustic images (this data path is indicated by the dashed line to cine memory 16 in FIG. 1), while other systems store the X-Y video images. The image stored in cine memory 16 can be reviewed on the display monitor via trackball control (interface 22), and a section of the image loop can be selected for hard disk storage.

For an ultrasound scanner with free-hand three-dimensional imaging capability, the selected image sequence stored in cine memory 16 is transferred to host computer 20 for three-dimensional reconstruction. The result is written back into another portion of the cine memory or to scan converter memory, from where it is sent to display 18 via the video processor 14.

Figure 2:
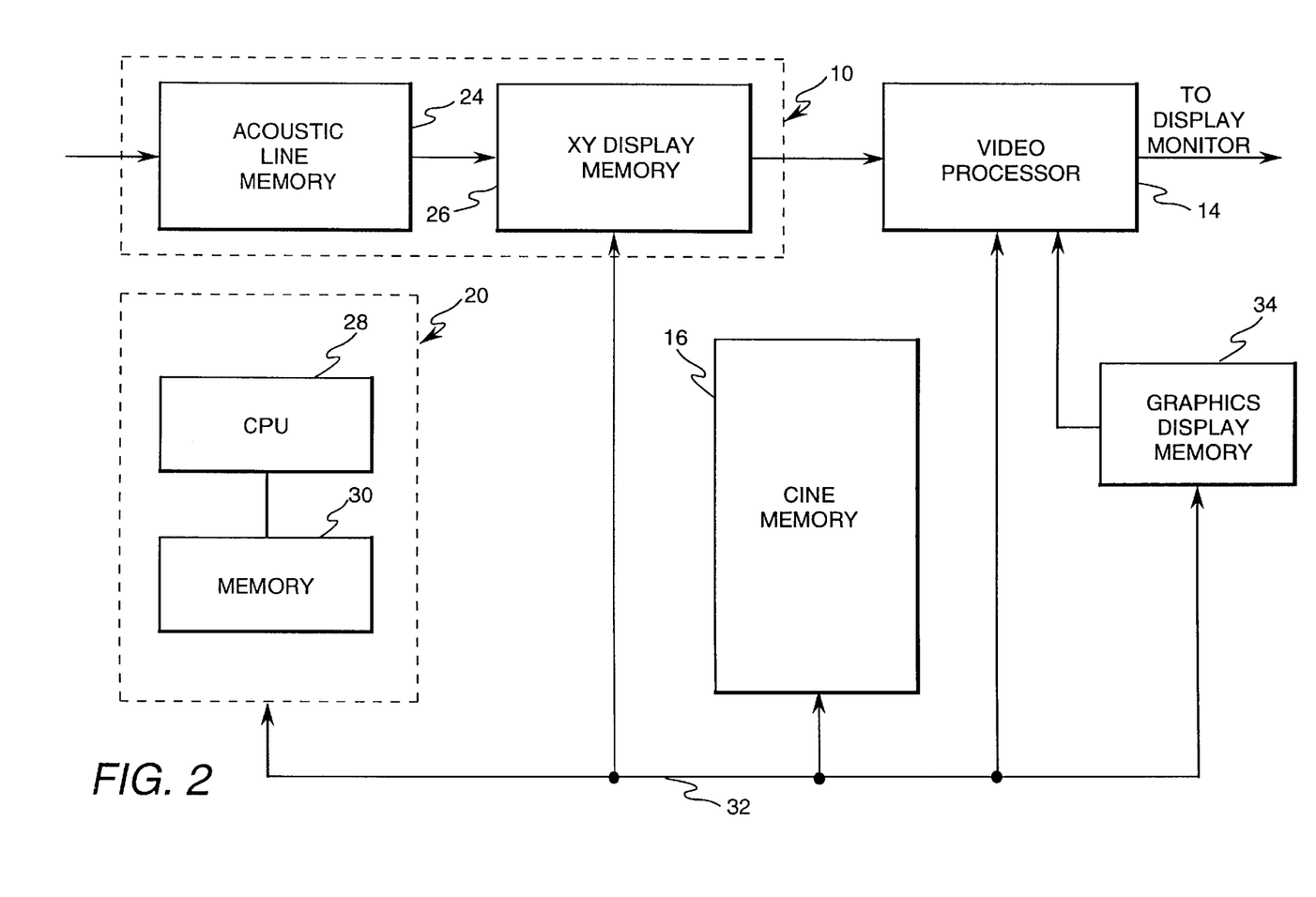
FIG. 2 is a block diagram showing the means for processing imaging data when any one of the three-dimensional imaging modes is selected.

In FIG. 2, scan converter 10 is seen to comprise an acoustic line memory 24 and an XY display memory 26. The B-mode imaging data stored in polar coordinate ($R$-$_\theta$) sector format in acoustic line memory 24 is transformed to appropriately scaled Cartesian coordinate intensity data, which is stored in XY display memory 26. Each image frame from XY display memory 26 is sent to video processor 14. Before gray mapping, frames of B-mode imaging data in video processor 14 are stored in cine memory 16 on a first-in, first-out basis. Storage can be continuous or as a result of an external trigger event. Cine memory 16 is, in effect, a circular image buffer that functions in the background, capturing image data that are displayed in real time to the user. When the user freezes the system (by operation of an appropriate device on the operator interface 22), the user has capability to view image data previously captured in cine memory.

The selected image sequence stored in cine memory 16 is transferred to host computer 20 for three-dimensional reconstruction. The multiple frames of imaging data acquired during the sweep of the probe form a three-dimensional data volume. Host computer 20 retrieves the region of interest from cine memory 16 and employs a volume rendering technique to reconstruct projected images onto various imaging planes. The projected data resulting from each projection are written back into another portion of the cine memory or to scan converter memory, from where they are sent to display monitor 18 via video processor 14.

Host computer 20 comprises a central processing unit (CPU) 28 and system memory 30. CPU 28 is programmed to transform an acquired volume of imaging data into a multiplicity of three-dimensional projection images taken at different angles. The CPU 28 controls the flow of data between XY display memory 26, video processor 14, cine memory 16 and the CPU itself via the system control bus 32. Each frame of imaging data, representing one of a plurality of scans or slices through the object being examined, is stored sequentially in the acoustic line memory 24, in XY display memory 26 and in video processor 14. Before gray mapping, frames of B-mode imaging data are sent from the video processor to cine memory 16. A stack of frames, representing the scanned object volume, is stored in cine memory 16, forming a source data volume. Once the source data volume has been acquired, CPU 28 can provide three-dimensional projections of the data as well as arbitrary slices through the source data volume.

The imaging system also has capability to superimpose graphical symbols on any ultrasound image. The superimposition of graphics on the image frame is accomplished in video processor 14, which receives the ultrasound image frame from XY display memory 26 and the graphics data from a graphics display memory 34. The graphics data are processed and supplied to graphics display memory 34 by host computer 20 or by a dedicated graphics processor (not shown).

Figure 3:
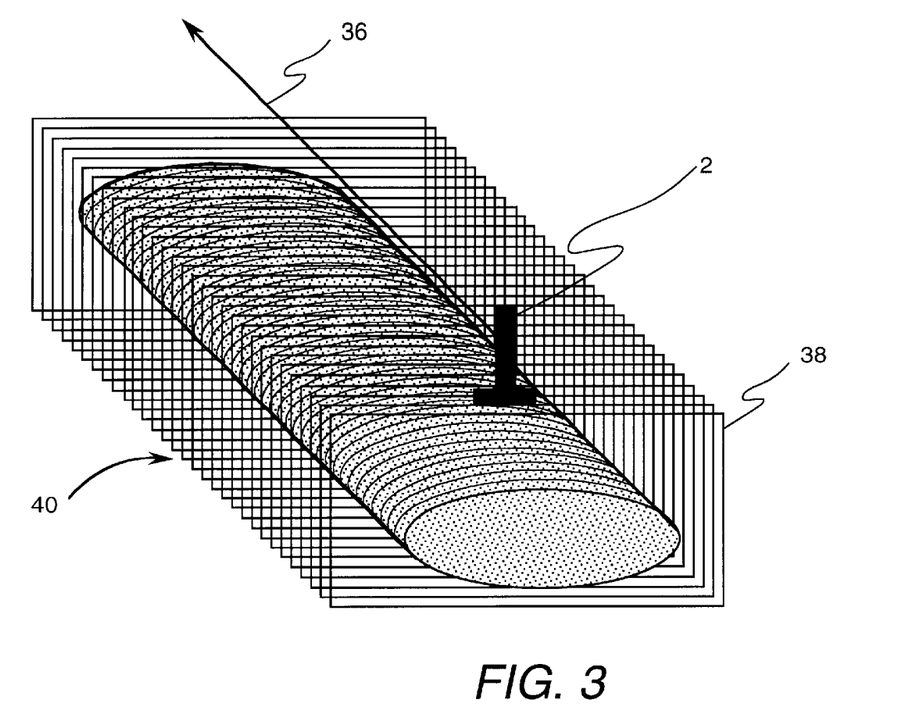
FIG. 3 is a diagram depicting a volume of data acquired by linearly scanning an ultrasound probe in a direction perpendicular to the scan plane of the probe.
Figure 4:
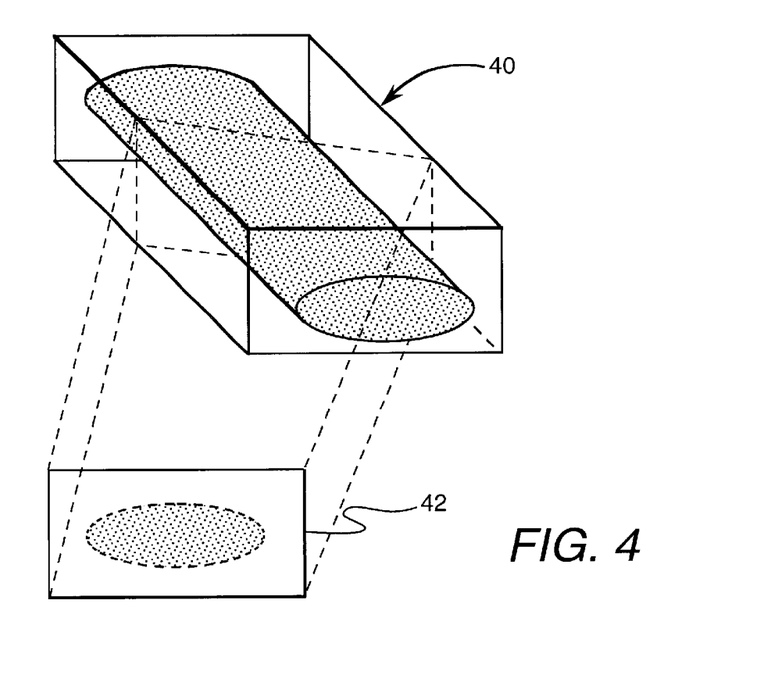
FIG. 4 is a diagram depicting an individual slice at an arbitrary angle obtained by reformatting the data volume depicted in FIG. 3.

FIG. 3 indicates that if ultrasound probe 2 is swept (arrow 36 indicates a linear sweep) over an area of a body (either by hand or by a probe mover), such that the inter-slice spacing is known, and if slices 38 are stored in memory, a three-dimensional data volume 40 can be acquired. The data volume can be processed (e.g., projected onto an imaging plane) to form a three-dimensional view of the area of interest. In addition, the data can be reformatted to produce an individual slice 42 at an arbitrary angle (see FIG. 4), thus allowing the user to obtain the exact view desired regardless of the anatomy under investigation. Algorithms for producing three-dimensional projections of two-dimensional data are well known, as are techniques for reformatting data to produce arbitrary slices through a data set. The problem that arises is how to display the information in a manner that enables the observer to easily relate the two-dimensional slice to the three-dimensional anatomy.

Figure 5:
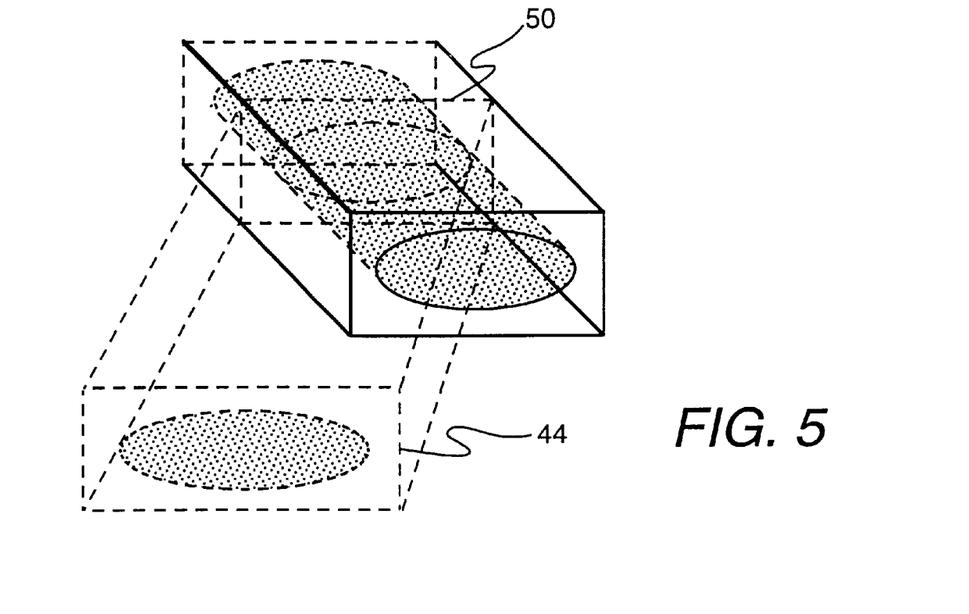
FIGS. 5–7 are diagrams depicting respective individual slices through orthogonal planes obtained by reformatting the data volume depicted in FIG. 3.
Figure 6:
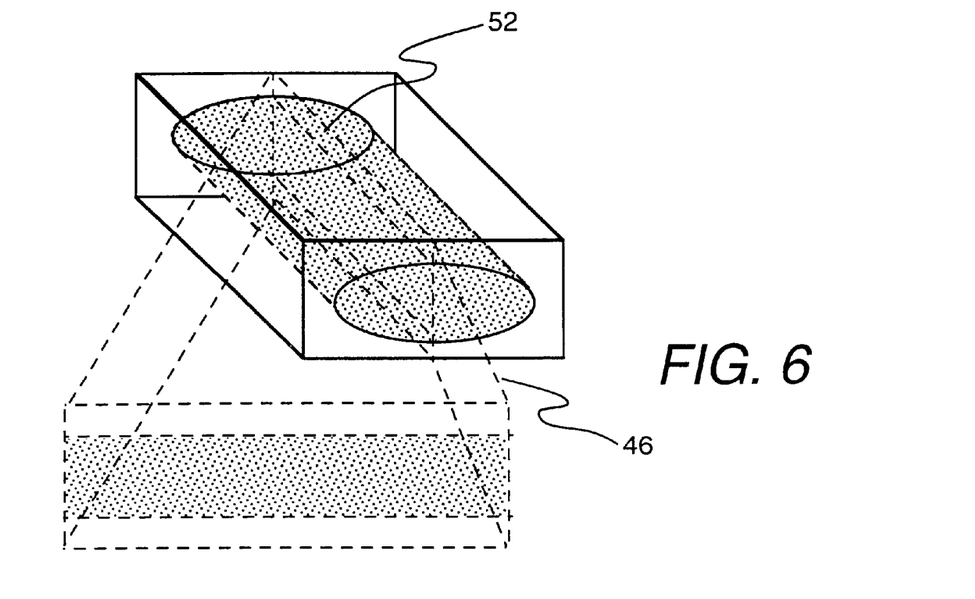
Figures 7, 8:
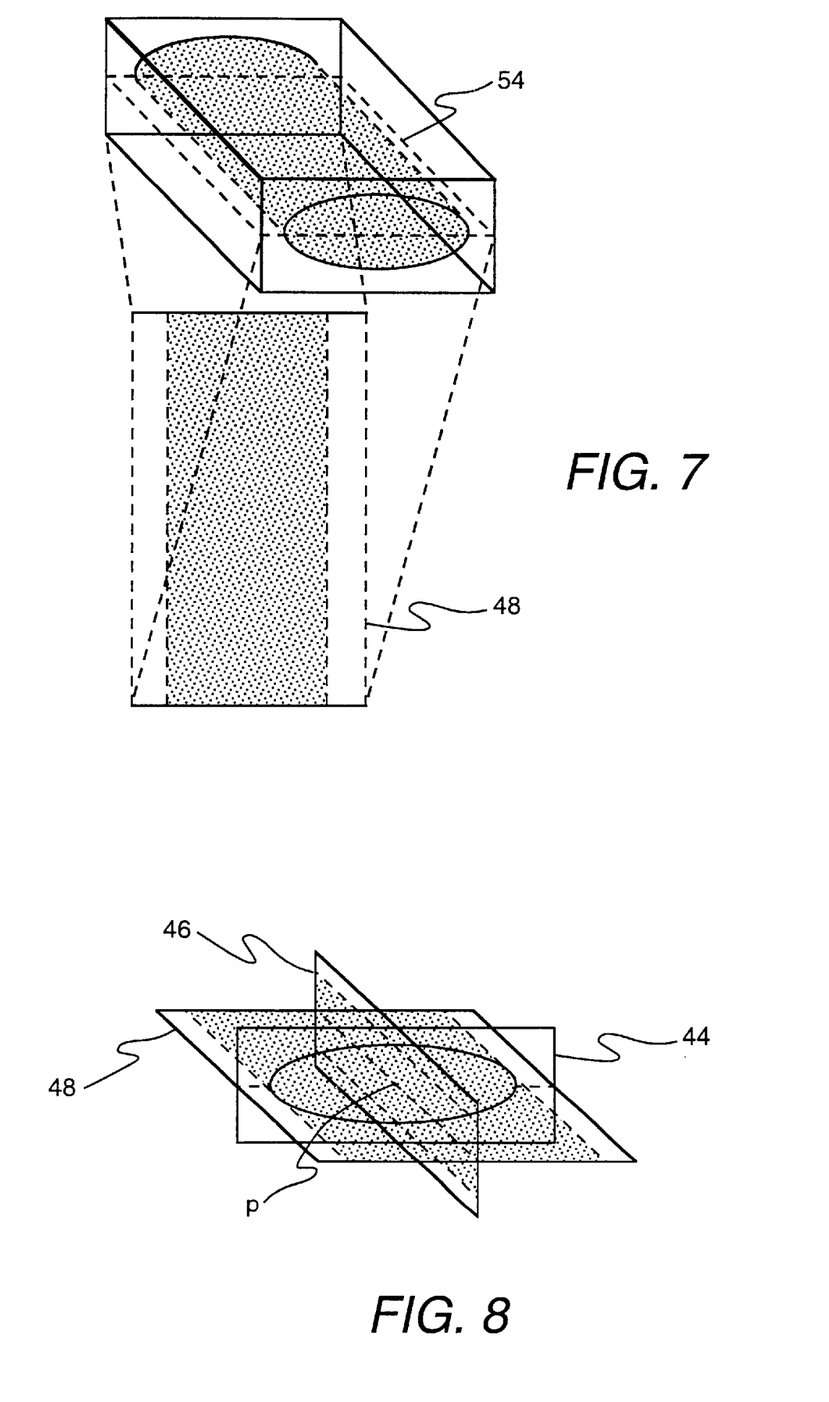
FIG. 8 is a diagram depicting the three slices of FIGS. 5–7 superimposed on a single point.

A preferred embodiment of the invention enables the system user to visualize how a slice through a data volume relates to non-parallel (e.g., orthogonal) slices through the same point in the data volume. FIGS. 5–7 depict respective individual slices 44, 46 and 48 of imaging data taken along respective mutually orthogonal planes 50, 52 and 54 intersecting at a point inside a data volume 40. FIG. 8 depicts the three slices 44, 46 and 48 of FIGS. 5–7 superimposed on a single point P at their intersection.

Figure 9:
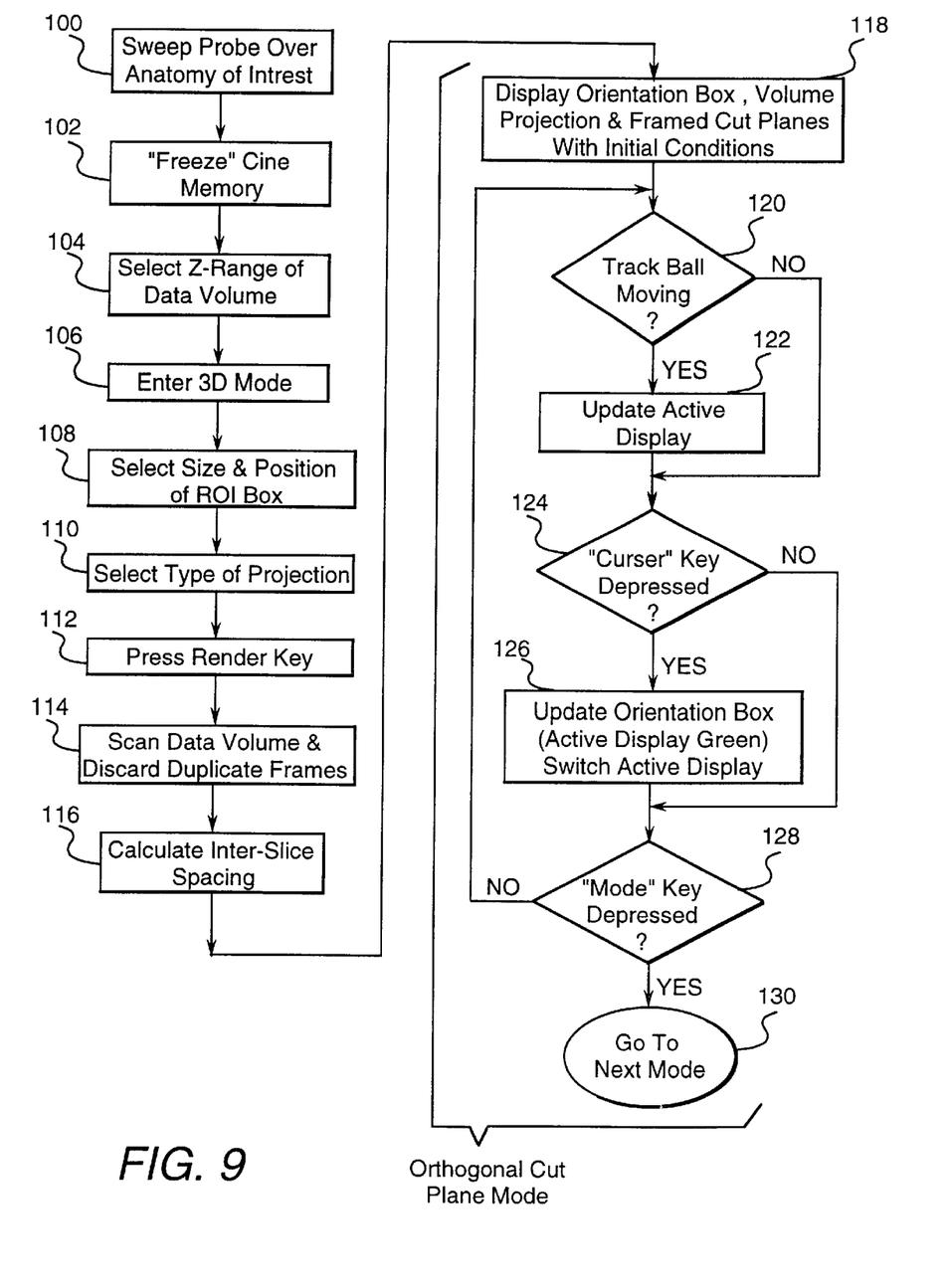
FIG. 9 is a flowchart of an acquisition and display procedure in accordance with a preferred embodiment of the invention.

FIG. 9 is a flowchart showing an acquisition and display procedure in accordance with a preferred embodiment of the invention. The user begins at step 100 by sweeping the ultrasound probe over an area of interest. The sweep may be acquired, for example, by a free-hand sweep in a linear or rocking motion. Once the data have been acquired, the user, at step 102, "freezes" the cine memory to maintain the data in place, as by depressing a Freeze key on the operator interface and then, at step 104, selects the range of cine memory frames (slices) to be included in the Z-dimension of the data volume. The operator accomplishes the latter step preferably by moving a trackball on the operator interface. A "Z-dimension select" gauge appears on the display screen when the trackball is moved. The trackball is then used to control the position of an indicator relative to the gauge. The operator moves the indicator to a desired left end point and then locks the left end point by depressing a predetermined key on the operator interface. The operator then move the indicator to a desired right end point and then locks the right end point by depressing the same predetermined key. This establishes the slices to be included in the data volume. The operator then enters the "3D model" at step 106 by depressing the appropriate key on the interface.

Upon entering the 3D mode, the operator must first select the XY-dimension and location of the region of interest (ROI) within the data volume (step 108). This selection is accomplished by manipulating a region of interest box which appears in a default position on the display screen when the 3-D mode key has been depressed. The region of interest box can be sized and translated in the X and Y directions to encompass an imaged structure which appears on a sector scan image. The region of interest box is translated by moving the trackball and is sized by operation of a four-sided rocker switch incorporated in the operator interface.

After the ROI has been defined, the operator, at step 110, selects the type of three-dimensional projection (minimum, maximum or average pixel projection, surface rendering, composite technique, etc.) desired, and then, at step 112, presses a render key. The defined ROI is then retrieved from cine memory 16 (see FIG. 2) by host computer 20. The host computer, at step 114, scans the retrieved data for duplicate frames and discards them and then, at step 116, calculates the inter-slice spacing for the data set. (The inter-slice spacing is assumed to be constant over the length of the data volume.) For example, the inter-slice spacing can be calculated using the adaptive speckle correlation technique disclosed in commonly assigned Larry Mo U.S. patent application Ser. No. 09/045,780 (15UL4625), filed on Mar. 20, 1998.

Figure 10:
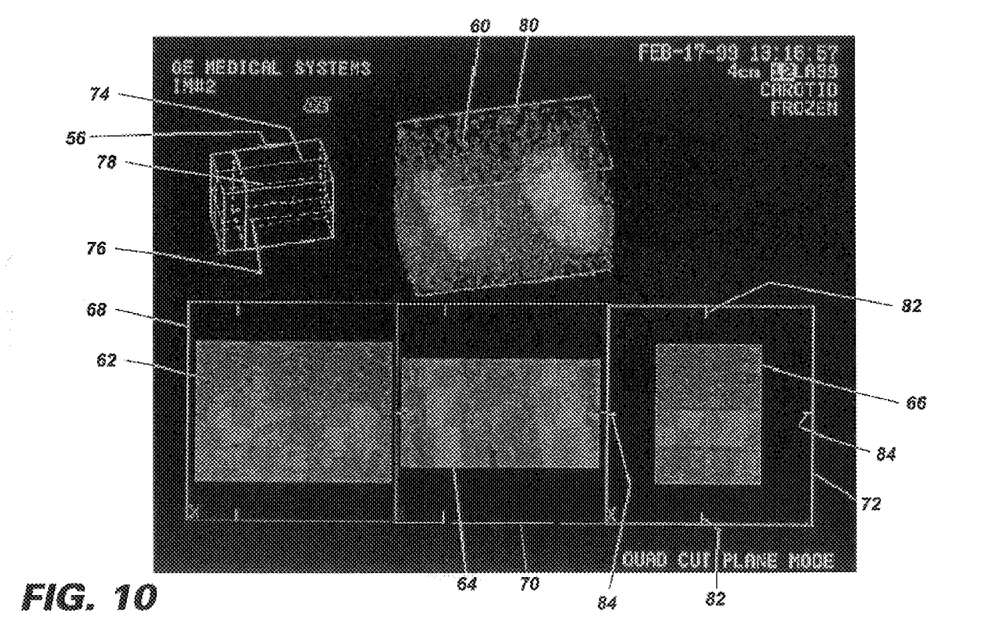
FIG. 10 illustrates a computer-generated image showing the multiple images displayed in the orthogonal cut plane mode in accordance with a preferred embodiment of the invention.

After calculation of the inter-slice spacing, the system enters an "orthogonal cut plane" mode, which is one of multiple submodes included in the 3D mode. Upon initialization of the "orthogonal cut plane" mode at step 118, signals representing a colored (e.g., green) orientation box having an initial orientation are generated by the host computer (or a dedicated graphics processor), arranged in XY format in graphics display memory 34 of FIG. 2 and then sent to video processor 14. The video processor causes a green orientation box 56 (see FIG. 10) to be displayed on a screen 58 of display 18 (see FIG. 1), the box having the initial orientation shown. At the same time, the host computer performs the selected full-resolution pixel projection of the defined data volume based on the calculated inter-slice spacing and the initial orientation. As apparent from FIG. 1, the projected three-dimensional image is sent to cine memory 16 and then on to video processor 14 which generates the projected three-dimensional image 60 for display, as shown in FIG. 10, on screen 58 along with orientation box 56. In the "orthogonal cut plane" display mode, the host computer also generates three images 62, 64 and 66 representing slices of data taken at mutually intersecting planes that are mutually orthogonal and intersect at a point in the data volume. These slices of data are also sent to the video processor for concurrent display, as shown in FIG. 10, with the orientation box and the projected three-dimensional image. In the initial state, the slices are taken at the mid-planes of the data volume. These initial positions of the cut planes are not depicted in FIG. 10.

In addition to the orientation box, other graphics are generated by host computer 20 of FIG. 2 (or a dedicated graphics processor) and sent to video processor 14 via graphics display 34. In particular, as shown in FIG. 10, cut plane image 62 is framed by a frame 68, cut plane image 64 is framed by a frame 70, and cut plane image 66 is framed by a frame 72. Each of frames 68, 70 and 72 has the same rectilinear or square shape, but is presented on the display monitor in a different color, e.g., red, blue and yellow. In accordance with a preferred embodiment of the invention, the positions of the three cut planes are indicated on orientation box 56 by respective parallelograms imaged in colors which match the colors of frames 68, 70 and 72. For example, a parallelogram 74 superimposed on orientation box 56 corresponds to and indicates the position of cut plane 62 being displayed inside frame 68, a parallelogram 76 superimposed on orientation box 56 corresponds to and indicates the position of cut plane 64 being displayed inside frame 70, and a parallelogram 78 superimposed on orientation box 56 corresponds to and indicates the position of cut plane 66 being displayed inside frame 72. Moreover, each parallelogram comprises two solid straight lines, indicating the intersection of the respective cut plane with surfaces of the data volume which are visible in projected image 60, and two dashed straight lines, indicating the intersection of the respective cut plane with hidden surfaces of the data volume shown in projected image 60.

In FIG. 10, the cut plane positions are also indicated by superimposing markers on frames 68, 70 and 72. Each frame has two pairs of markers, each pair of markers indicating the position of a respective one of the other two cut planes, i.e., the cut planes not displayed within that particular frame. For example, frame 72 has a first pair of markers 82 which indicate the position of the cut plane for image 62, and a second pair of markers 84 which indicate the position of the cut plane for image 64. Preferably, the markers are presented in colors that match the colors of the frames for the cut planes whose positions are being indicated. For example, if frame 68 were depicted in red, frame 70 in blue and frame 72 in yellow, then markers 82 would be depicted in red and markers 84 in blue. Thus, for each cut plane image, the corresponding frame, cut plane graphic on the orientation box 56, and position markers on the other two frames are depicted in a respective color.

In addition to the above-described cut plane position graphics, straight lines 80 outlining the visible faces of the data volume are superimposed on projected image 60 in a color different than the colors of frames 68, 70 and 72 and different than the color (i.e., green) used to denote the so-called "active" display, to be disclosed in detail below.

The orthogonal cut plane mode displays four images (60, 62, 64 and 66 in FIG. 10) and a wire-frame orientation box 56. However, only one of the four display images is "active" at any time. The term "active display" as used herein means the display which can be manipulated using an interface device, e.g., a trackball.

When the volume projection image 60 is the active display, the projected image can be rotated by manipulating the trackball, i.e., the data volume projection is updated in real-time. The initial rendering in this display mode is a full-resolution projection. As the user manipulates the trackball, the orientation box follows the rotation and the volume projection is decimated by a predetermined factor to achieve real-time reconstruction that will follow trackball movement. When the user stops moving the trackball, a projection in the extant orientation is re-rendered at full resolution (i.e., without decimation).

When one of the cut plane images 62, 64 or 66 is the active display, the user can scroll through the data volume in the selected orientation by manipulating the trackball, i.e, the selected cut plane image can be translated along the axis perpendicular to that cut plane.

In the initial state, the volume projection image 60 is the active display. Subsequently, the active display is switched to the next display image in response to each depression of a cursor key on the operator interface. For example, the active display may be programmed to cycle sequentially through volume projection image 60, the XY cut plane image 62, the ZX cut plane image 64, and the ZY cut plane image 66 in response to successive depressions of the cursor key.

The active display is indicated on the orientation box by a unique color, e.g., green. If the volume projection image is active, then the wire-frame of orientation box 56 will be green. In the initial state, the volume projection image is active. If the cursor key is depressed, the wire frame changes color from green to the color of the graphic outline 80 superimposed on volume projection image 60 and the color of the appropriate cut plane graphic 74, 76 or 78 on the orientation box changes to green, as does its corresponding frame 68, 70 or 72, respectively. Thus, the active display is always indicated by the same color, which is selected to be different than the other colors used in the orthogonal cut plane display mode.

The foregoing algorithm is generally depicted in the flowchart of FIG. 9. After initialization of the orthogonal cut plane display mode at step 118, the host computer at step 120 determines whether the trackball (or other interface device) is moving. If the trackball is moving, then the active display is updated at step 122. After the active display has been updated, the host computer at step 124 determines whether the cursor key has been depressed. The host computer also performs step 124 in response to a determination at step 120 that the trackball is not moving.

If the cursor key on the operator interface is depressed, then the active display is switched at step 126 to the next display image in the programmed sequence. In addition, the orientation box is updated by changing to green the color of the lines indicating the new active display image and changing from green to its characteristic color the color of the lines indicating the no longer active display image. After the active display has been switched, the host computer determines, at step 128, whether the mode key has been depressed. The host computer also performs step 128 in response to a determination at step 124 that the cursor key is not depressed.

If, at step 128, it is determined that the mode key is not depressed, the host computer recyles back to step 120 and again determines whether the trackball is moving. The sequence comprising steps 120, 122, 124, 126 and 128 is repeated until the host computer determines that the mode key is depressed, at which point the program exits the orthogonal cut plane display mode at step 130 and enters the next 3D mode in a programmed sequence of modes.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. An imaging system comprising:
   a display subsystem for displaying images; and a computer programmed to control said display subsystem to concurrently display in spaced relationship a three-dimensional projection image representing a projection of a data volume at a certain orientation, a first cut plane image representing a first planar cut through said data volume, a first graphic comprising a geometric representation of said data volume at said certain orientation and a second graphic comprising a geometric representation of said first cut plane, said second graphic having a positional relationship to said first graphic corresponding to the positional relationship of said first cut plane to said data volume;

and wherein said computer is further programmed to control said display subsystem to concurrently display a second cut plane image representing a second planar cut through said data volume and a third graphic comprising a geometric representation of said second cut plane, said third graphic having a positional relationship to said first graphic corresponding to the positional relationship of said second cut plane to said data volume, wherein said first and second cut planes are not parallel.

2. The system as recited in claim 1, wherein said first graphic is displayed in a first color and said second graphic is displayed in a second color different than said first color.

3. The system as recited in claim 2, wherein said computer is further programmed to control said display subsystem to concurrently display a first frame in spaced relationship to said first cut plane image, wherein said first frame is displayed in said second color.

4. The system as recited in claim 1, wherein said first and second cut planes are orthogonal.

5. The system as recited in claim 1, wherein said first graphic is displayed in a first color, said second graphic is displayed in a second color and said third graphic is displayed in a third color, said first, second and third colors being different from each other.

6. The system as recited in claim 5, wherein said computer is further programmed to control said display subsystem to concurrently display a first frame in spaced relationship to said first cut plane image and a second frame in spaced relationship to said second cut plane image, wherein said first frame is displayed in said second color and said second frame is displayed in said third color.

7. The system as recited in claim 6, wherein said first and second cut planes are mutually orthogonal, and said computer is further programmed to control said display subsystem to concurrently display a position marker in a positional relationship to said first frame corresponding to the positional relationship of said second cut plane to said first cut plane.

8. The system as recited in claim 7, wherein said position marker is displayed in said third color.

9. The system as recited in claim 1, wherein said computer is further programmed to control said display subsystem to concurrently display a third cut plane image representing a third planar cut through said data volume and a fourth graphic comprising a geometric representation of said third cut plane, said fourth graphic having a positional relationship to said first graphic corresponding to the positional relationship of said second cut plane to said data volume, wherein said first, second and third cut planes are mutually not parallel.

10. The system as recited in claim 9, wherein said first, second and third cut planes are mutually orthogonal.

11. The system as recited in claim 1, further comprising a first operator interface device, wherein said computer is further programmed to control said display subsystem to display reconstructed images of said three-dimensional projection image in real-time while said operator interface device is being manipulated if said three-dimensional projection image is active, and to display reconstructed images of said first cut plane image in real-time while said first operator interface device is being manipulated if said first cut plane image is active.

12. The system as recited in claim 11, further comprising a second operator interface device, wherein said computer is further programmed to change the state of said three-dimensional projection image from active to inactive, and to change the state of said first cut plane image from inactive to active in response to manipulation of said second operator interface device.

13. The system as recited in claim 12, wherein said first graphic is displayed in a first color and said second graphic is displayed in a second color when said three-dimensional projection image is active and said first cut plane image is inactive, and said first graphic is displayed in a third color and said second graphic is displayed in said first color when said three-dimensional projection image is inactive and said first cut plane image is active.

14. A method for displaying images, comprising the step of concurrently displaying in spaced relationship a three-dimensional projection image representing a projection of a data volume at a certain orientation, a first cut plane image representing a first planar cut through said data volume, a first graphic comprising a geometric representation of said data volume at said certain orientation and a second graphiccomprising a geometric representation of said first cut plane, said second graphic having a positional relationship to said first graphic corresponding to the positional relationship of said first cut plane to said data volume;

and wherein said step of concurrently displaying further comprises concurrently displaying second and third cut plane images respectively representing second and third planar cuts through said data volume, and third and fourth graphics respectively comprising geometric representations of said second and third cut planes, said third and fourth graphics having respective positional relationships to said first graphic corresponding to the respective positional relationships of said second and third cut planes to said data volume, wherein none of said first, second and third cut planes are parallel.

15. The method as recited in claim 14, wherein said first, second and third cut planes are mutually orthogonal.

16. The method as recited in claim 14, wherein said first through fourth graphics are respectively displayed in first through fourth different colors, and said step of concurrently displaying further comprises concurrently displaying first through third frames in respective spaced relationship to said first through third cut plane images, said first through third frames being displayed in said second through fourth colors respectively.

17. The method as recited in claim 16, wherein the step of concurrently displaying further comprises concurrently displaying a position marker in a positional relationship to said first frame corresponding to the positional relationship of said second cut plane to said first cut plane.

18. The method as recited in claim 17, including the step of displaying said position marker in said third color.

19. The method as recited in claim 14, further comprising the steps of:

activating said three-dimensional projection image;

manipulating a first operator interface device while said three-dimensional projection image is active;

displaying reconstructed images of said three-dimensional projection image in real-time during manipulation of said first operator interface device while said three-dimensional projection image is active;

changing said three-dimensional projection image from active to inactive and said first cut plane image to active;

manipulating said first operator interface device while said first cut plane image is active; and displaying reconstructed images of said first cut plane image in real-time during manipulation of said first operator interface device while said first cut plane image is active.

20. The method as recited in claim 19, wherein said first graphic is displayed in a first color and said second graphic is displayed in a second color while said three-dimensional projection image is active, and said first graphic is displayed in a third color and said second graphic is displayed in said first color while said first cut plane image is active, said first, second and third colors being different from each other.

21. The method as recited in claim 19, wherein the step of changing said three-dimensional projection image from active to inactive and said first cut plane image to active comprises the step of manipulating a second operator interface device.

\* \* \* \* \*